United States Patent [19]

Hansen

[11] 4,177,188

[45] Dec. 4, 1979

[54] PROCESS FOR RECOVERING PURIFIED ALBUMIN FROM BLOOD PLASMA USING PEG AND CAPRYLIC ACID

[75] Inventor: Jørgen F. Hansen, Rødovre, Denmark

[73] Assignee: Nordisk Insulinlaboratorium, Gentofte, Denmark

[21] Appl. No.: 868,253

[22] Filed: Jan. 10, 1978

[30] Foreign Application Priority Data

Jan. 21, 1977 [DK] Denmark ............................ 258/77

[51] Int. Cl.² ............................................. C07G 7/00
[52] U.S. Cl. .................................... 260/122; 424/101; 424/177
[58] Field of Search ............................ 260/112 B, 122

[56] References Cited

U.S. PATENT DOCUMENTS

| | | | |
|---|---|---|---|
| 2,705,230 | 3/1955 | Reid | 260/112 B |
| 2,765,299 | 10/1956 | Porsche et al. | 260/122 |
| 3,415,804 | 12/1968 | Polson | 260/112 B |
| 3,790,552 | 2/1974 | Johnson et al. | 260/112 B |
| 3,926,939 | 12/1975 | Ivanov et al. | 260/122 |
| 3,992,367 | 11/1976 | Plan et al. | 260/122 |
| 4,017,470 | 4/1977 | Izaka et al. | 260/122 |
| 4,025,500 | 5/1977 | Garcia et al. | 260/112 B |

FOREIGN PATENT DOCUMENTS

1480184 7/1977 United Kingdom.

OTHER PUBLICATIONS

Monogr. Allergy, vol. 12, pp. 27-35 (1977), Ring et al.
Kirk-Othmer, p. 562, vol. 2 (1948).

*Primary Examiner*—Howard E. Schain
*Attorney, Agent, or Firm*—Ladas, Parry, Von Gehr, Goldsmith & Deschamps

[57] ABSTRACT

A process is disclosed for the recovery of albumin in very high purity from human blood plasma by treatment of the blood plasma with polyethylene glycol (PEG) to precipitate out impurities followed by thermocoagulation of a resulting supernatant aqueous solution containing PEG and albumin in the presence of caprylic acid and isolation of the purified albumin by precipitation.

3 Claims, No Drawings

PROCESS FOR RECOVERING PURIFIED ALBUMIN FROM BLOOD PLASMA USING PEG AND CAPRYLIC ACID

The present invention relates to a process for recovering purified albumin by fractional precipitation of blood plasma.

Albumin has previously been isolated from blood plasma by fractional precipitation with alcohols, such as ethanol, at low temperatures, and by precipitation in saline solutions, for example by stepwise addition of ammonium sulphate. These known processes have various drawbacks. Thus, precipitation with ethanol entails a tendency to denature the protein with a subsequent reduction of the yield, and saline precipitations give impure products as no sharp separation is obtained.

The specification of the U.S. Pat. No. 3,415,804 teaches a process of fractional precipitation of protein mixtures in the presence of polyethylene glycol (PEG), the polyethylene glycol inhibiting the dispersibility of the proteins. This process which has been used for fractioning human blood plasma, has given a number of fractions, including an albumin fraction, which, however, was contaminated with betaglobulin and other proteins. Thus, it has not been possible to obtain a satisfactorily purified albumin for thereapeutical use by this known process.

From the Danish Patent Application No. 1252/75 it is known to isolate albumin from blood and similar products by heating the albumin containing liquid in the presence of an alcohol and albumin stabilizing substances. Caprionates are mentioned as one example among many of stabilizing substances for this purpose. However, it has not been possible to avoid completely the drawbacks of the ethanol or similar alcohols to denature proteins.

Furthermore, it is known from the Danish Published Application No. 134 425 to prepare albumin by subjecting a solution of albumin, such as placenta or human blood plasma, to a thermocoagulation in the presence of caprylic acid ions at temperatures between 52 and 64° C. and a pH-value between 4.8 and 5.25. During termocoagulation hemoglobin, denatured albumin and foreign proteins are precipitated. The purified albumin remains in the solution from where it may be recovered.

However, this known process gives a rather impure product. The purity can be improved by carrying out a fractional precipitation prior to the thermocoagulation, for example with trichloroacetic acid and ethanol, but a pure product suitable for therapeutical use cannot be achieved in this manner.

A thermocoagulation is also known from the British Patent Specification No. 739 024, but not in connection with a preceding PEG-precipitation.

The present invention is based on the recognition that it is possible in a simple manner and without adding alcohols to combine a fractional precipitation of albumin in the presence of PEG with a heat treatment in the presence of caprylic acid as stabilizer, resulting in a coagulation of the impurities which otherwise would precipitate together with the albumin. Thus, there is obtained a high yield of albumin with a high degree of purity.

The process of the invention is thus characterized in that blood plasma is admixed with polyethylene glycol (PEG) and adjusted to a pH of 6 to 7 for precipitating fibrinogen and globulins, that the supernatant with a content of 150 to 300 g PEG, preferably 180–200 g, per liter liquid is adjusted to a pH of 4.5 to 5.3 for precipitating albumin, that the albumin with entrained PEG is redissolved in an aqueous medium, that the resulting albumin solution is subjected to a thermocoagulation at 50 to 65° C. and a pH of 4.6 to 5.0 in the presence of a stabilizing amount of caprylic acid, and that the purified albumin is isolated from the solution by precipitation. In the subject process stabilized blood plasma is used to which PEG is added in an amount suitable for the precipitation, for example 150 to 300 g per liter; PEG 4000 is suitable, but higher or lower molecular weights may be employed, such as 1000 to 50000. The preferred amount is 180 to 200 g PEG per liter liquid.

The precipitation of the globulin containing fraction is carried out, as mentioned, at a pH of 6 to 7, but the optimum pH is about 6.7. The precipitate is expediently separated by centrifuging, and the albumin containing solution centrifuged-off is then adjusted to a pH of 4.5 to 5.3, preferably 4.9, whereby an albumin containing fraction is precipitated. This fraction contains some proteins, impurities as well as PEG. The precipitate is redissolved in water, for example in a concentration of about 80 g/l. Then there is added caprylic acid, expediently in an amount of 2 to 3 g/l, for example 2.5 g/l. The solution is adjusted to a pH of 4.6 to 5.0, expediently 4.8, and then heated to 50 to 65° C., preferably about 60° C., a suitable period of heating being about 30 minutes.

By this heat treatment the majority of the protein impurities still present is coagulated during precipitation. If such a heat treatment was carried out at a temperature above about 55° C. without addition of caprylic acid the albumin would be decomposed, and the yield would be dissatisfactorily low. The product is cooled after the heat treatment, and the coagulate is separated by centrifuging or filtration. The purified albumin from the centrifuged or filtered solution is isolated by precipitation in a manner known per se. Thus, ethanol, preferably 40%, may be added, and the purified albumin is precipitated at a pH of 4.8 and by cooling to a temperature below 0° C. This albumin is collected, for example by centrifuging, and freeze dried.

The process of the invention has the advantage that an extremely pure product of albumin with a high yield can be produced in a simple manner. Furthermore, the subject process entails another advantage, viz. that it is capable of industrial working. In the process the denaturing of the globulins is avoided which means that the fractions containing these proteins can be further processed to obtain valuable globulins in a high yield and in a pure state.

Though PEG precipitations and thermocoagulations have been known separately, no attempts have been made till now to combine these methods of purification. Such a combination makes it possible to avoid denaturing the albumin which undoubtedly explains the high yield. However, it has not been possible to foresee that a substantially improved purity of the product is obtained at the same time.

Still another advantage of the process according to the invention is that blood plasma is used as starting material. This is possible because the globulins, as mentioned, are not denatured which means that they may be processed in a high yield.

The process of the invention will be illustrated in greater detail below by means of an example.

EXAMPLE 100 l of citrate-stabilized human blood plasma were admixed with 137 l of 33% weight of an aqueous solution of polyethylene glycol 3000 to obtain 19% PEG in the solution. The pH-value was adjusted to 6.7±0.1. The mixture was left to stand for 45 minutes and then centrifuged. The precipitate consisted of fibrinogen and globulin. The supernatant contained the albumin. The albuminous supernatant was admixed with acetic acid to a pH=5.0 to 4.8.

The resulting precipitate consisting of albumin was centrifuged off. The albumin was redissolved in 80 l of distilled water at about 40° C., and 200 ml caprylic acid were added. The pH-value was adjusted to 4.8±0.1 with a solution of 1 M NaOH in water. The solution was heated to 60±0.5° C. for 30 minutes. The resulting precipitate was centrifuged off. The centrifuged solution was precipitated with cold ethanol (40% ethanol, −5° C., pH=4.8).

The precipitated albumin was centrifuged-off and freeze dried. After redissolving in distilled water, addition of 0.04 M caprylic acid, and adjustment of pH to 7.0±0.4 the solution was bottled, heat treated at 60° C. for 10 hours and then it was suitable for therapeutical use. The content of high molecular substances, that is to say the fraction having a molecular weight above 200,000 g/mole, is less than 0.1% of the total amount of proteins. The yield of albumin is about 90% of the albumin contained in the plasma.

A scanning of the albumin by means of dyed polyacrylamide electrophoresis showed a purity not below 99.5%.

What I claim is:

1. A process for recovering purified albumin suitable for intravenous injection from human blood plasma without denaturing the globulins present therein, comprising the steps of:
    (a) mixing the blood plasma with 150 to 300 g polyethylene glycol (PEG) per liter of liquid mixture and adjusting the mixture to a pH of 6 to 7 for precipitating fibrinogen and globulins while forming a supernatant containing albumin;
    (b) separating the supernatant from the formed precipitate;
    (c) adjusting the pH of the supernatant to a pH of 4.5 to 5.3; for precipitating albumin;
    (d) redissolving the albumin with entrained PEG in an aqueous medium;
    (e) subjecting the resulting albumin solution formed during step (d) to thermocoagulation at 50 to 65° C. and a pH of 4.6 to 5.0 in the presence of a stabilzing amount of caprylic acid; and
    (f) isolating the purified albumin from the solution by precipitation.

2. A process according to claim 1, wherein PEG is used in an amount of 180 to 200 g PEG per liter liquid supernatant obtained after precipitating fibrinogen and globulins.

3. A process according to claim 1, wherein the caprylic acid is used in an amount of 2 to 3 g caprylic acid per liter of the solution of albumin during the thermocoagulation.

* * * * *